United States Patent [19]

Strauss

[11] Patent Number: 4,552,137
[45] Date of Patent: * Nov. 12, 1985

[54] EARPLUGS

[76] Inventor: Richard H. Strauss, 1501 Doone Rd., Columbus, Ohio 43221

[*] Notice: The portion of the term of this patent subsequent to Aug. 17, 1999 has been disclaimed.

[21] Appl. No.: 523,422

[22] Filed: Aug. 16, 1983

[51] Int. Cl.$^4$ .............................................. A61F 11/02
[52] U.S. Cl. ................................................. 128/152
[58] Field of Search ................ 128/151, 152, 153, 156

[56] References Cited

U.S. PATENT DOCUMENTS

| | | | |
|---|---|---|---|
| 968,008 | 8/1910 | Waller | 128/152 |
| 2,574,288 | 11/1951 | Rosenblatt | 128/152 |
| 2,716,625 | 8/1955 | Scholl | 128/153 |
| 3,487,832 | 1/1970 | Spence | 128/153 |
| 3,771,521 | 11/1973 | Kittredge | 128/152 |
| 3,881,570 | 5/1975 | Lewis | 128/152 |
| 4,344,425 | 8/1982 | Strauss | 128/152 |

Primary Examiner—Henry J. Recla
Attorney, Agent, or Firm—Cushman, Darby & Cushman

[57] ABSTRACT

An earplug in the form of a preformed self-supporting body of malleable plastic material which is deformable under slight pressure, the body having a front face and a rear face, the front face having a generally convex surface adapted to conform to and cover the opening of the ear canal and the body having a size such that it is adapted to reside within the external ear when the generally convex surface is positioned over the opening of the ear canal, and a layer of pressure-sensitive adhesive so located on the convex surface as to releasably adhere the surface to the periphery of the ear canal opening.

6 Claims, 8 Drawing Figures

EARPLUGS

This invention relates to earplugs or ear protectors for excluding the entry of material and/or sound waves into the ear canal.

BACKGROUND

Earplugs are used to prevent entry of foreign material, especially water, into the ear canal. They are also used to prevent or reduce entry of sound waves, thereby providing auditory protection or assisting the wearer in sleeping. Such plugs are usually designed to fit into the ear canal to be engaged more or less tightly by the wall of the canal inside the entrance area thereof to frictionally hold the plug in place. They remain in place because they are wedged into the ear canal, and they tend to leak, fall out or irritate the canal because of the wedge pressure.

In addition to these well known types of rubber or foamed plastic plugs that are designed for frictionally engaging the walls of the canal, there are other kinds of plugs such as one made of a putty-like silicone resin body shaped into a form for insertion into the canal to form an earplug, the resin being encased in a flexible envelope to aid its insertion into the canal where it likewise is held in place by frictional engagement with the wall of the canal. This type of earplug is described in U.S. Pat. No. 3,771,521.

Another somewhat similar plug is shown in U.S. Pat. No. 4,160,449, where a foam plastic encased in a thin flexible envelope is utilized to hold the foam compressed during insertion into the canal, the compressed foam being released upon insertion in the canal to expand and engage the wall of the canal.

As an alternative to a plug engaged within the ear canal, U.S. Pat. No. 4,134,153 discloses a bag-like structure for enclosing the entire ear. The bag is attached to the head with a pressure sensitive adhesive. U.S. Pat. No. 2,574,288 discloses an ear protector in the form of a wax body which spans the entrance to the ear canal and when lightly pressed in place by a finger becomes slightly softened by the heat of the flesh and conforms itself to the shape of the part of the ear against which it has been pressed.

All of these known means have defects in use and are either uncomfortable to wear over long periods of time or do not, in the case of the bag-type seal, provide a very effective seal. Swimmers may move through the water rapidly or may be subjected to rough treatment by breakers during ocean bathing and such vigorous water action may wash away frictionally held plugs or the bag-type of ear enclosure. Further, if the more popular frictionally supported plugs are used during periods of highly active swimming and diving for example, the plugs must be tightly engaged in the ear canal and soon become very uncomfortable to wear.

My U.S. Pat. No. 4,344,425 discloses improvements over the earlier earplugs.

BRIEF DESCRIPTION OF THE INVENTION

The present invention provides an earplug in the form of a self-supporting body of soft deformable material having a generally convex surface which carries a pressure sensitive adhesive for releasably attaching the plug to the ear and for forming a seal with the skin. The plug does not rely on friction developed by compression of the plug body as it is inserted into the ear canal, and therefore the plug need not fit tightly into the canal. The plug therefore is comfortable when worn for long periods of time and does not irritate the ear canal. In some embodiments the plug may essentially overlie the ear canal, rather than being inserted into the canal. In either case the adhesive surface engages the mouth of the ear canal and forms a seal therewith sufficient to prevent entry of foreign material and/or sound waves and sufficient to hold the plug in place even during, for example, surf bathing.

The material of the self-supporting body of the plug is plastic in the sense of being pliable and deformable or moldable by slight pressure. A particularly useful material is a malleable silicone plastic material of the Silly Putty variety. Alternative materials include natural and synthetic rubber and soft pliable plastics in general, but these are not preferred unless they are malleable in the sense of being easily deformable and having the ability to retain their deformed shape after removal of the deforming force.

The material may be foamed or unfoamed and may contain fillers. One type of material may be used as a core and another type, particularly a malleable material, may be used as a covering on the core. By self-supporting and malleable is meant that the body at rest tends to retain a preformed shape resulting from deformation of the material of the body and/or from its manufacture. The body is thus not a film but is a discrete plug-like mass having a substantial thickness. If the material is a foam it may be closed-cell or open-cell and in the latter case the surface of the plug may be sealed to render it water proof or it may be provided with a thin covering of liquid-impermeable material such as plastic film. The material may be selected to provide or exclude sound transmission. In general the Silly-Putty type of material will exclude sound transmission whereas foam material will transmit sound.

At least part of the outer surface of the earplug is sufficiently convex to approximately fit the opening of the ear canal but not so convex to permit any significant entry of the plug into the canal. This characteristic, together with the deformable nature of at least the outer covering of the plug, assures that an annular portion of the surface will closely approximate the contours of an individual ear canal opening without relying on a friction fit between the surface of the ear canal and the surface of the earplug. Thus, when the plug is in place, essentially all of the plug resides within the external ear.

A pressure-sensitive adhesive is provided on at least that portion of the convex surface of the plug which contacts the ear canal opening. This, together with the deformable nature of the plug material assures that an annular seal will be formed between the ear canal opening and the plug and that the plug will be held in place. The composition of the adhesive may be conventional.

DETAILED DESCRIPTION

Figures 1, 2, 4:
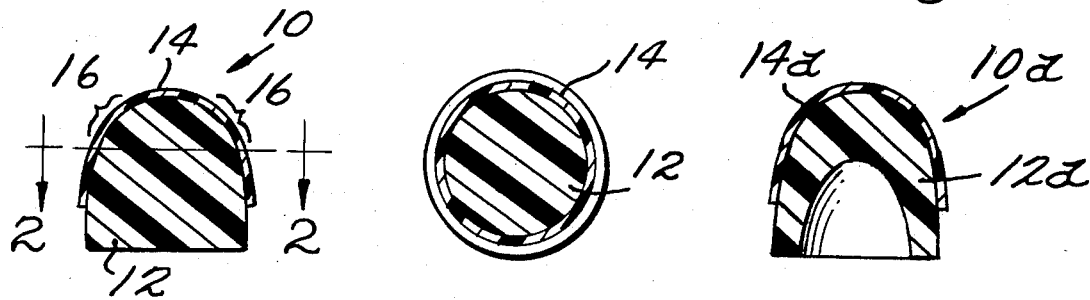
FIG. 1 is a longitudinal sectional view of a first embodiment of an earplug embodying the principles of the present invention.
FIG. 2 is a transverse cross section of the earplug taken on the line 2—2 of FIG. 1.
FIGS. 4, 5, 6, 7 and 8 are longitudinal cross sectional views of second, third, fourth, fifth and sixth embodiments, respectively, of the earplug.

FIGS. 1 and 2 illustrate an earplug 10, according to the invention, in which the required outer convex surface is generally bullet-shaped in that it has a generally spherical front end portion which merges into a rear end portion of conical or cylindrical shape.

The body 12 of the earplug 10 is a solid plug of malleable silicone resin material, such as Silly Putty material, which has been preformed or preshaped to the illustrated shape. The shape of the rear surface of the earplug 10 is not important. In most of the embodiments illustrated herein this surface is flat, but it may be of any shape. As the rear end portion will be grasped by the fingers when manipulating the earplug 10, this portion may be shaped to provide a finger tab or a finger tab may be attached thereto.

A layer of pressure-sensitive adhesive 14 is provided on the convex front surface of the earplug 10. The thickness of the adhesive 14 relative to the size of the body 12 has been exaggerated for purposes of illustration. The required minimum area of the adhesive 14 is an annular area, illustrated at 16 in FIG. 1, which will contact the external acoustic meatus or ear canal opening. Typically, however, the adhesive 14 will be carried on a major portion of the convex surface of the body. A removable protective film (not shown) may be provided on the adhesive 14 to prevent contamination of the adhesive prior to use.

Figure 3:
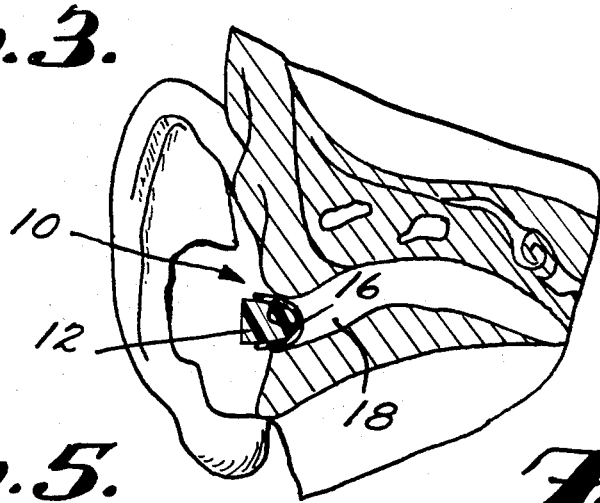
FIG. 3 is a sectional view showing the earplug of FIG. 1 in place in an ear.

FIG. 3 illustrates the operative position of the earplug 10 in an ear. It will be seen that the convex front surface of the earplug 10 contacts an annular portion of the skin at the opening of the ear canal 18 and that there is no or essentially no contact with the ear canal itself. Thus, there is essentially no frictional engagement of the plug 10 with the ear canal 18. Rather, when the plug 10 is pressed lightly into place by the wearer's fingers, the malleable plug body 12 molds itself to the contour of the particular ear canal opening and is held in place by the pressure-sensitive adhesive. The diameter of the front portion of the plug 10 is such that the annular area 16 of cantact between the adhesive 14 and ear canal opening is close to the front end of the plug 10. If the ear canal opening is larger than the one illustrated, the annular contact area 16 will be somewhat to the rear of the illustrated position. In any event, essentially the entire plug 10 resides within the external ear.

FIG. 4 illustrates an ear plug 10a which is generally similar to that of FIG. 1 except that the rear face of the plug 10a is concave. That is, the plug 10a has generally the shape of a hollow cone with a rounded front portion.

Figures 5, 6:
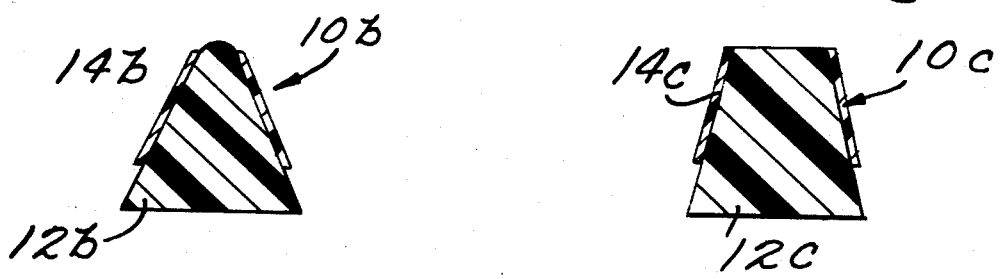

FIG. 5 illustrates an earplug 10b of conical shape and FIG. 6 illustrates an earplug 10c of frusto-conical shape.

Figures 7, 8:
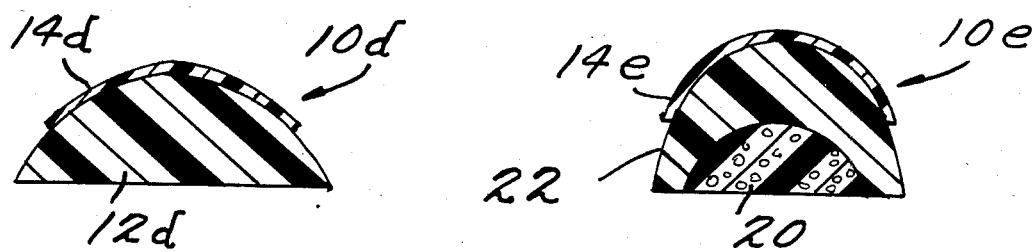

FIG. 7 illustrates an earplug 10d of semicylindrical shape.

FIG. 8 illustrates an earplug 10e having an overall shape similar to the plug 10 of FIG. 1 but being of multicomponent construction. The plug body 12e is made of a body 20 of resilient plastic foam to which is adhered an outer covering 22 of malleable plastic material. The adhesive 14e is provided on the malleable covering 22.

What is claimed is:

1. An earplug comprised of a preformed self-supporting body of resilient elastomeric material selected from the group consisting of foamed and unfoamed rubber and foamed and unfoamed synthetic plastics material, said body having a front face and a rear face, said front face having a generally convex forward surface adapted to conform to and cover the opening of the ear canal and a rearward surface and said body having a size such that it is adapted to reside within the external ear when said generally convex surface is positioned over the opening of the ear canal, and a layer of pressure sensitive adhesive on said generally convex surface for releasably adhering the body to the periphery of the ear canal opening.

2. An earplug as in claim 1 wherein said rearward surface of said front face of said body is conical or frusto-conically shaped and continuous with said generally convex surface.

3. An earplug as in claim 1 wherein said generally convex surface is generally spherical.

4. An earplug as in claim 1 wherein the adhesive layer is in the form of a ring.

5. An earplug as in claim 1 wherein said rearward surface of said front face of said body is frusto-conically shaped and continuous with said generally convex surface.

6. An earplug comprised of a preformed self-supporting body of malleable plastic material which is deformable under slight pressure, said body having a front face and a rear face, said front face exhibiting a generally convex surface adapted to conform to and cover the opening of the ear canal and said body having a size such that it is adapted to reside within the external ear when said generally convex surface is positioned over the opening of the ear canal, and a layer of pressure-sensitive adhesive so located on said generally convex surface as to releasably adhere said surface to the periphery of the ear canal opening.

* * * * *